United States Patent
Li et al.

(10) Patent No.: US 8,633,689 B2
(45) Date of Patent: Jan. 21, 2014

(54) NMR FLOW METERING USING VELOCITY SELECTION AND REMOTE DETECTION

(75) Inventors: Lilong Li, Humble, TX (US); Songhua Chen, Katy, TX (US); Carl M. Edwards, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 479 days.

(21) Appl. No.: 12/971,740

(22) Filed: Dec. 17, 2010

(65) Prior Publication Data

US 2012/0092007 A1    Apr. 19, 2012

Related U.S. Application Data

(63) Continuation-in-part of application No. 12/907,707, filed on Oct. 19, 2010.

(51) Int. Cl.
*G01V 3/00* (2006.01)

(52) U.S. Cl.
USPC .......................................................... 324/306

(58) Field of Classification Search
USPC .......................... 324/300–322; 600/407–435; 382/128–131
See application file for complete search history.

(56) References Cited

U.S. PATENT DOCUMENTS

| | | | |
|---|---|---|---|
| 4,536,711 A | 8/1985 | King et al. | |
| 4,785,245 A | 11/1988 | Lew et al. | |
| 6,046,587 A | 4/2000 | King et al. | |
| 6,452,390 B1 | 9/2002 | Wollin | |
| 6,549,007 B1 | 4/2003 | Hills et al. | |
| 6,822,454 B2 | 11/2004 | Peck et al. | |
| 6,952,096 B2 | 10/2005 | Freedman | |
| 7,126,332 B2 | 10/2006 | Blanz et al. | |
| 7,141,978 B2 | 11/2006 | Peck et al. | |
| 7,186,971 B2 | 3/2007 | Riley et al. | |
| 7,501,819 B2 | 3/2009 | Ong | |
| 7,719,267 B2 | 5/2010 | Pusiol | |
| 2004/0015332 A1 | 1/2004 | Martin et al. | |
| 2005/0140368 A1* | 6/2005 | Freedman | 324/306 |
| 2005/0189945 A1 | 9/2005 | Reiderman | |
| 2005/0216196 A1 | 9/2005 | Akkurt et al. | |
| 2006/0020403 A1 | 1/2006 | Pusiol | |
| 2007/0114996 A1 | 5/2007 | Edwards | |
| 2007/0164737 A1 | 7/2007 | Pusiol | |
| 2008/0174309 A1 | 7/2008 | Pusiol et al. | |
| 2008/0174313 A1 | 7/2008 | Ganesan | |
| 2008/0186024 A1 | 8/2008 | Edwards | |
| 2010/0264916 A1 | 10/2010 | Pusiol | |

OTHER PUBLICATIONS

Carbon-13 NMR, available at http://en.wikipedia.org/wiki/Carbon-13_NMR on Feb. 21, 2010.*

(Continued)

*Primary Examiner* — Melissa Koval
*Assistant Examiner* — Daniel Miller
(74) *Attorney, Agent, or Firm* — Mossman Kumar & Tyler PC (57) ABSTRACT

A method and apparatus for estimating a flow rate of a phase of a multiphase fluid is disclosed. In the first method, nuclei in the fluid are polarized over two distances and a measured magnetization gives the relative fraction of two components of the fluid for a selected velocity. In the second method, nuclei in the fluid are polarized over a specified distance and measurements of the decay of spin echo signals is used to give the relative fraction of two components of the fluid for the selected velocity.

26 Claims, 5 Drawing Sheets

(56) References Cited

OTHER PUBLICATIONS

Proton NMR, available at http://en.wikipedia.org/wiki/Proton_NMR on Mar. 5, 2010.*

H.Y.Carr et al., "Effects of Diffusion on Free Precession in Nuclear Magnetic Resonance Experiments," Physical Review, vol. 94, No. 3, May 1, 1954, pp. 630-638.

S. Meiboom et al., "Modified Spin-Echo Method for Measuring Nuclear Relaxation Times," Review of Scientific Instruments, vol. 29, No. 8, Aug. 1958, pp. 688-691.

A. Caprihan et al., "Flow Measurements by NMR," Physics Reports (Physics Letters) 198, No. 4, 1990, pp. 195-235.

G.J. Kruger et al., "Nuclear magnetic resonance (NMR) two-phase mass flow measurements," Flow Meas. Instrum., vol. 7, No. 1, Nov. 28, 1994, pp. 25-37.

* cited by examiner

NMR FLOW METERING USING VELOCITY SELECTION AND REMOTE DETECTION

CROSS-REFERENCES TO RELATED APPLICATIONS

This application is a continuation in part of U.S. patent application Ser. No. 12/907,707 filed on Oct. 19, 2010.

BACKGROUND OF THE DISCLOSURE

Multiphase fluid flows are common in pipes used in the transport of hydrocarbons for the petroleum industry. The current disclosure is directed to a method of using time of flight measurements to select a portion of the fluid that flows at a certain velocity. The velocity selection is accomplished by NMR spin-echo method. Difference in spin-lattice relaxation time $T_1$ and spin-spin relaxation time $T_2$ for different phases are used to differentiate the signal contribution from the different phases, thus making it possible to estimate the flow rate for each individual phase.

SUMMARY OF THE DISCLOSURE

One embodiment of the disclosure is a method of estimating a flow rate of a phase of a fluid having a plurality of components. The method includes: using a magnet for polarizing nuclei of the fluid flowing over a plurality of distances wherein a number of the distances is equal to or greater than a number of the components; measuring a magnetization of the polarized nuclei for each of the plurality of distances for a selected flow velocity; using the plurality of measured magnetizations for estimating a relative fraction of each of the plurality of components corresponding to the selected velocity.

Another embodiment of the disclosure is an apparatus configured to estimate a flow rate of a phase of a fluid having a plurality of components. The apparatus includes: a magnet configured to polarize nuclei of the fluid flowing over a plurality of distances wherein a number of the distances is equal to or greater than a number of the components; a coil arrangement configured to measure a magnetization of the polarized nuclei for each of the plurality of distances for a selected flow velocity; a processor configured to use the plurality of measured magnetizations to estimate a relative fraction of each of the plurality of components corresponding to the selected velocity.

Another embodiment of the disclosure is a method of estimating a flow rate of a phase of a fluid having a plurality of components. The method includes: using a magnet for polarizing nuclei of the fluid flowing over a selected distance; pulsing the polarized nuclei with a tipping pulse with a first coil, a refocusing pulse with a second coil at a first distance from the first coil, a refocusing pulse with a third coil at a second distance from the first coil, and measuring an echo signal for each of the plurality of distances for a selected flow velocity; using the plurality of echo signals for estimating a relative fraction of each of the plurality of components corresponding to the selected velocity.

Another embodiment of the disclosure is an apparatus configured to estimate a flow rate of a phase of a fluid having a plurality of components. The apparatus includes: a magnet configured to polarize nuclei of the fluid flowing over a selected distance; a first coil arrangement configured to pulse the polarized nuclei with a tipping pulse, a second coil at a first distance from the first coil configured to pulse the polarized nuclei with a refocusing pulse, the third coil at a second distance from the first coil configured to pulse the polarized nuclei with a refocusing pulse, and at least one additional coil configured to measure and echo signal for each of the plurality of distances for a selected flow velocity; and a processor configured to use the plurality of echo signals to estimate a relative fraction of each of the plurality of components corresponding to the selected velocity.

BRIEF DESCRIPTION OF THE DRAWINGS

For detailed understanding of the present disclosure, reference should be made to the following detailed description, taken in conjunction with the accompanying drawings, in which like elements have been given like numerals and wherein.

DETAILED DESCRIPTION

Figure 1:
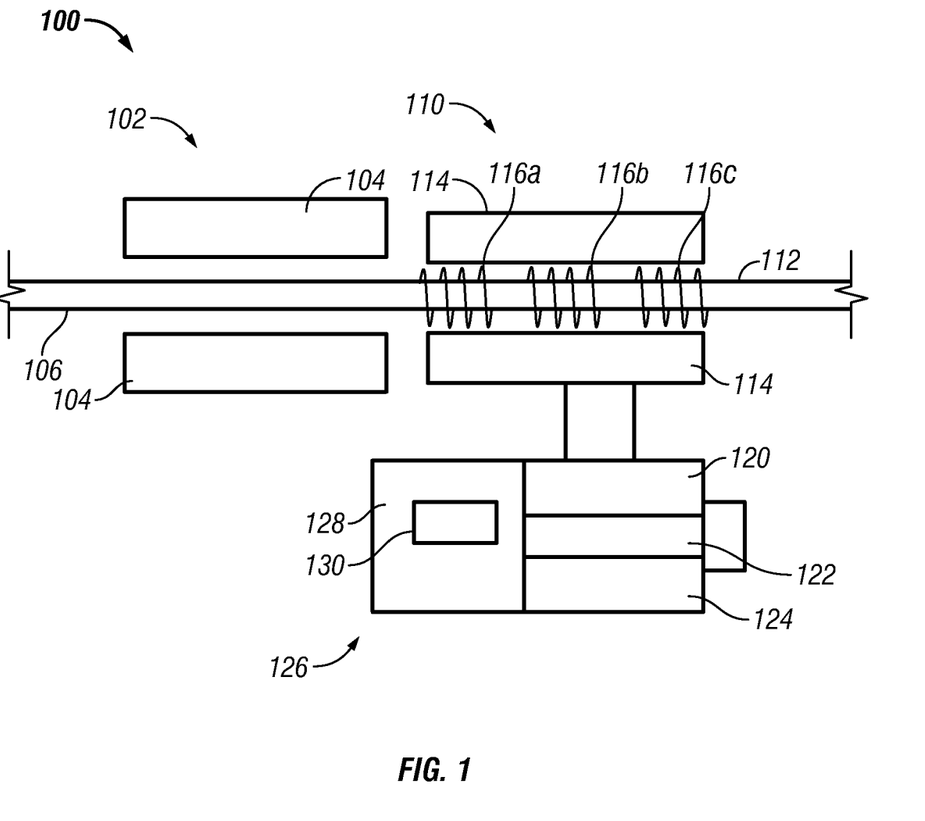
FIG. 1 shows an exemplary Nuclear Magnetic Resonance (NMR) flow meter device for estimating a flow rate of a fluid phase in a conduit using an exemplary method of the present disclosure.

FIG. 1 shows an exemplary Nuclear Magnetic Resonance (NMR) flow meter device 100 for estimating a flow rate of a fluid phase using an exemplary method of the present disclosure. In one embodiment, the fluid may be a multiphase fluid. In another embodiment, the fluid may be a fluid flowing in a conduit for transportation of hydrocarbons. The exemplary NMR flow meter 100 may include a pre-polarization section 102 for polarizing nuclear spins of fluid along a selected direction, a detection section 110 for applying NMR excitation pulses to the fluid and obtaining NMR signals in response to the NMR excitation pulses from the fluid. The apparatus also includes a testing unit 126 for receiving the NMR response signals from the detection section 110 and performing calculations on the received NMR response signals to obtain a flow rate of a phase of the fluid.

In the illustrative example of FIG. 1, fluid flows from left to right so as to flow from pre-polarization section 102 into the detection section 110. The pre-polarization section 102 includes a conduit 106 and a pre-polarization magnet 104 which may be exterior to the conduit 106 in one embodiment. The pre-polarization magnet 104 is arranged so as to provide a static magnetic field in a volume of the pre-polarization pipe section 106, generally along a direction substantially axially along the pipe section 106. As fluid passes through the static magnetic field, nuclear spins of atoms and molecules within the fluid align along the direction of the static magnetic field.

Continuing with FIG. 1, detection section 110 is downstream of the pre-polarization section 102 and receives polarized fluid from the pre-polarization section 102. The detection section 110 includes a conduit 112, a detection magnet 114 which may be exterior to the detection pipe section 112 for providing a static magnetic field in a volume of the conduit 112, and a plurality of radio frequency (RF) coils 116a, 116b, 116c. The diameter of the conduit 112 is the same as the diameter of the conduit 106. The RF coil 116 encloses a volume within the conduit 112 and is arranged to provide one or more NMR excitation pulses to the fluid in the detection section 110 and to detect one or more NMR response signals from the fluid in the detection section 110.

Testing unit 126 includes various circuitry for obtaining one or more NMR response signals from the fluid and estimating a flow rate of a phase of the fluid from the obtained NMR response signals. The exemplary testing unit 126 is coupled to the RF coil 116 via preamplifier 120. The exemplary testing unit 126 includes a transmitter 124 for providing an NMR excitation pulse to the plurality of RF coils 116a, 116b, 116c via preamplifier 120. In one embodiment, the transmitter 124 provides multiple NMR excitation pulse sequences, each NMR excitation pulse sequence tuned to a selected nuclear resonance frequency. In one aspect, a first nuclear resonance frequency is that of the nuclei of $H^1$ atoms and a second nuclear resonance frequency is that of the nuclei of $C^{13}$ atoms. The exemplary testing unit 126 also includes a receiver 122 for receiving NMR response signals detected at the RF coil 116a, 116b, 116c via the preamplifier 120. Testing unit 126 also includes an NMR spectrometer 128 for estimating one or more parameters of the fluid from the received NMR response signals using exemplary methods of the present disclosure. In one embodiment, the spectrometer 128 may include a processor 130 configured to execute instructions contained in a program stored on a suitable storage device (not shown), such as a solid-state memory, tape or hard disc for storing the one or more parameters obtained at the processor 130.

The pre-polarization conduit 106 of FIG. 1 may include multiphase fluid flowing through a conduit 106. In the most general case, three phases may be present: water, oil and gas. Each phase of the fluid has a characteristic flow velocity profile. As would be known to those versed in the art, a fluid or fluid phase under laminar flow exhibits a velocity profile that has a slow section at the boundaries of the fluid and a fast section typically away from the boundaries. In general, the fast section of the fluid passes through a pipe section before the slowest portion does. The speed of the fluid affects a degree of alignment of the nuclei of the fluid. Nuclear alignment occurs over a characteristic time, as described below with respect to Eqn. (1). When a fluid is flowing in a volume of a static magnetic field, the slow portion of the fluid remains in the volume longer. It should be noted that the method of the present disclosure is not restricted to laminar flow and may also be used for turbulent flow as well as flow in which one phase is mixed with another phase. An example of this would be gas bubbles in oil, gas bubbles in water, water droplets in an oil phase as well as oil droplets in a water phase. This is in contrast to many prior art methods which are directed towards laminar flow in which each lamina consists substantially of only one phase.

Figure 2:
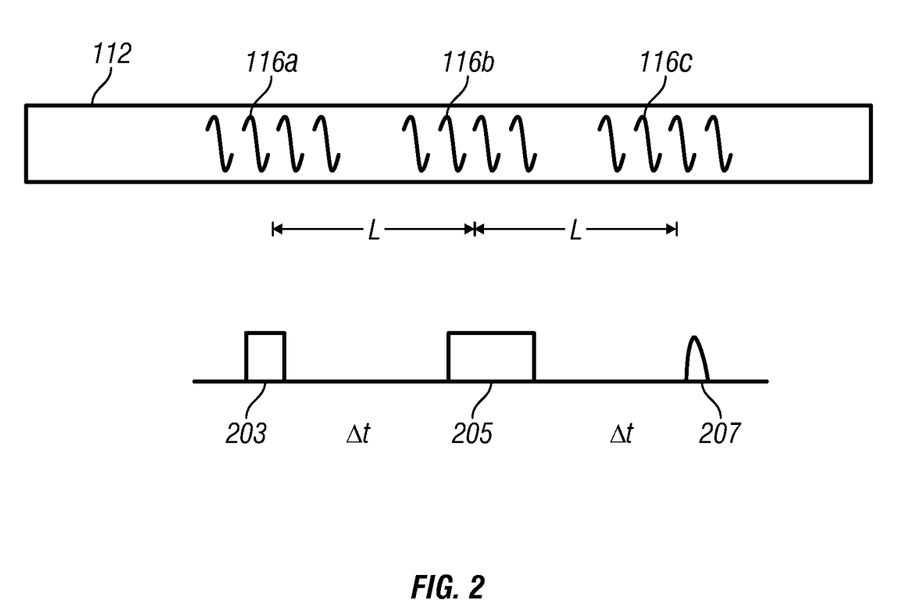
FIG. 2 shows exemplary applied pulses and echo for the apparatus of FIG. 1.

After passage through the pre-polarization section 100 nuclei in the fluid are polarized with their spins substantially oriented in the longitudinal direction. These polarized nuclei pass into the detection section 110. FIG. 2 illustrates the pulsing and an echo signal that can be obtained using the apparatus of FIG. 1. In the apparatus shown in FIG. 1, the magnetic field in the detection section is uniform and oriented in a longitudinal direction along the conduit 112. A 90° tipping pulse, indicated by 203, may be applied to the first coil 116a. This 90° tipping pulse results in the nuclei being tipped by 90°. These nuclei flow near the second coil 116b where a 180° refocusing pulse may be applied. This is not intended to be a limitation and additional refocusing coils and refocusing pulses may be provided. The coil 116c receives and echo signal denoted by 207. The distance between two coils is denoted by L and the time interval between the 90° pulse and the 180° pulse (and the 180° pulse and the echo) is denoted by Δt. In the example shown, only one refocusing pulse 205 (and refocusing coil 116b and receiving coil 116c are shown). When the length of the coil l is sufficiently smaller than the length L between coils, we may consider that the echo signal shown in FIG. 2 only comes from the part of the fluid that moves with velocity L/Δt. By varying the time Δt between pulses, the entire velocity spectrum can be mapped out. It should also be noted that the tipping pulse is not restricted to 90° and refocusing pulse is not restricted to 180°.

In one embodiment of the disclosure, the magnetic field in the pre-polarization section 100 may be produced by a switchable permanent magnet. Such a magnet is disclosed in U.S. patent application Ser. No. 11/037,488 (US20050189945). Disclosed therein is a coil coupled with a current source and a magnetic core having residual magnetization. Switching current in the antenna coil results in magnetization reversal in the magnetic core and reversal of the magnetic field. The advantage of the switchable permanent magnet is the relatively low power requirement for reversing the magnetic field and altering the polarization of nuclear spins.

Figure 3:
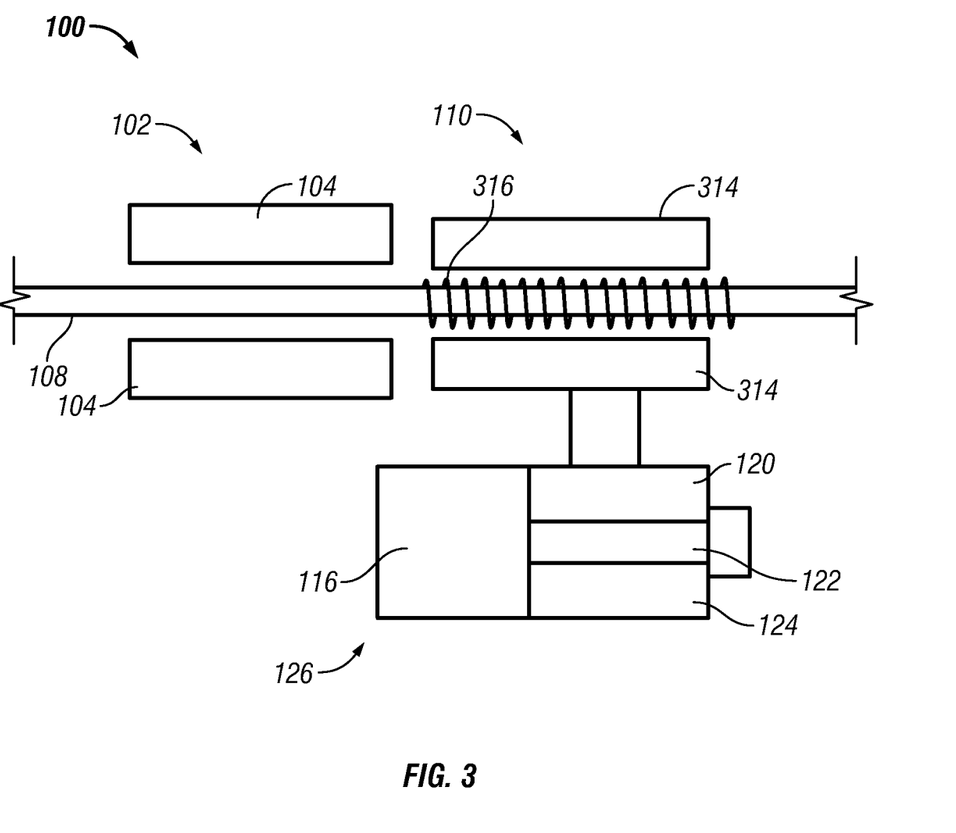
FIG. 3 shows an exemplary Nuclear Magnetic Resonance (NMR) flow meter device for estimating a flow rate of a fluid phase in a conduit using another exemplary method of the present disclosure that has a single coil.
Figure 4:
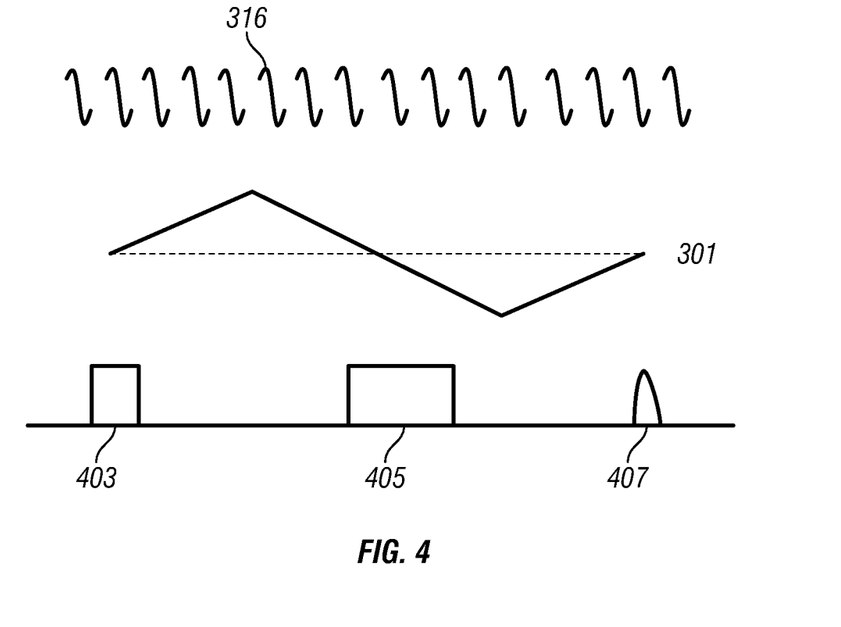
FIG. 4 shows exemplary magnetic field, applied pulses and echo for the apparatus of FIG. 2.

FIG. 3 shows an alternate embodiment of the disclosure in which instead of a plurality of coils as in FIG. 1, a single coil 316 is used. The axial variation of the magnitude of the axial static magnetic field is illustrated by 301. The 90° tipping pulse is shown by 403 in FIG. 4, the 180° refocusing pulse is shown by 405, and the echo is shown by 407. By varying the external magnetic field, as shown here, the locations on resonance are restricted to a few points along the pipe and thus the length of the flow within Δt is certain. In an alternate embodiment of the disclosure, instead of varying the static magnetic field, a pulsed field gradient may be applied in the detection section.

The multi-coil design FIG. 1 can be expanded. For example, in FIG. 5, a fourth coil 516d is added at length 2L after coil 516c. Now coil 516c not only receives the echo signal, but also can transmit a 180° refocusing pulse and coil 516d receives the echo. Such a setup will increase the efficiency of data gathering. Next, differentiation of the different phases of the fluid in the conduit using the apparatus described above is discussed.

Figure 5:
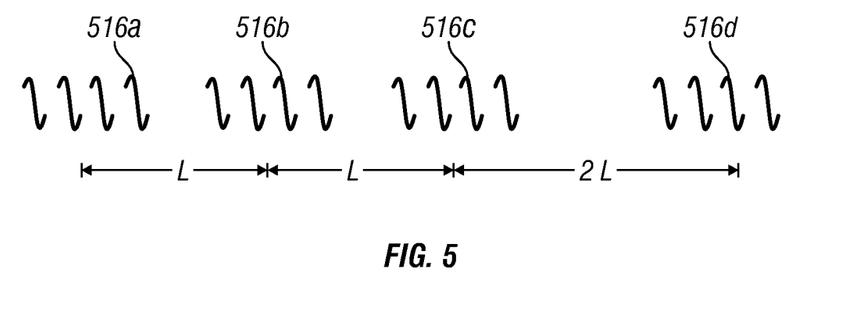
FIG. 5 shows an arrangement with four coils.

Phase differentiation may be achieved by multiple measurements with varying prepolarization length or varying flow length in the measurement region, as the one shown in FIG. 5. The magnetization buildup inside the prepolarization magnet, for a fluid flowing at velocity v is $$M_i = M_{0,i}(1 - e^{-L_p/vT_{1,i}}) \quad (1),$$

where $M_i$ is the magnetization of the i-th phase to be detected by NMR measurement, $M_{0,i}$ is the maximum prepolarization achievable, which is proportional to the amount of protons in the i-th phase, $L_p$ is the prepolarization length, and $T_{1,i}$ is the proton spin-lattice relaxation time for i-th phase.

As an example, consider two phases in the conduit and two measurements being made with two prepolarization lengths, $L_{p1}$ and $L_{p2}$. The NMR measured magnetization S is a combination of the contribution from two separate phases:

$$S_1 = M_{0,1}(1 - e^{-L_{p1}/vT_{1,i}}) + M_{0,2}(1 - e^{-L_{p1}/vT_{1,2}})$$

$$S_2 = M_{0,1}(1 - e^{-L_{p2}/vT_{1,i}}) + M_{0,2}(1 - e^{-L_{p2}/vT_{1,2}}) \quad (2).$$

Here, $L_{p1}$ and $L_{p2}$ are known, v is the velocity that is selected, $T_{1,1}$ and $T_{1,2}$ are the properties of the phases and can be characterized, $S_1$ and $S_2$ are the measured signals, so $M_{0,1}$ and $M_{0,2}$ can be solved in the above equations. $M_{0,1}$ and $M_{0,2}$ are indicative of the relative fraction of the two components flowing at the selected velocity. Thus two phases can be differentiated and the flow rate can be obtained. This is illustrated in the flow chart of FIG. 6.

Figure 6:
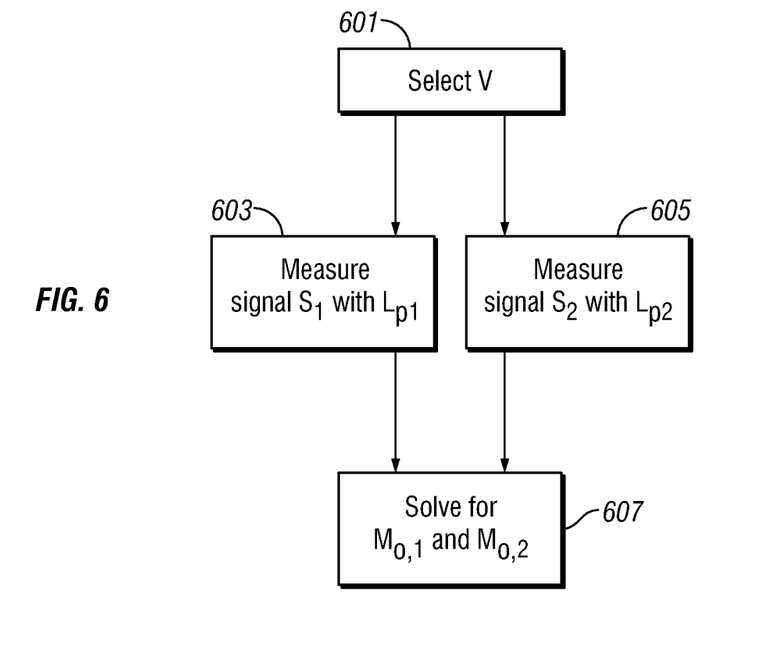
FIG. 6 shows a flowchart of a method of the present disclosure using two different pre-polarization lengths.

A velocity v is selected 601. This defines the value of $\Delta t$ used with the coil separation L in the measurement section. For the value of $\Delta t$, a signal $S_1$ is measured 603 with the first pre-polarization length $L_{p1}$. For the same value of $\Delta t$, a signal $S_2$ is measured 605 with the second pre-polarization length $L_{p2}$. Solution of the eqn. (2) 607 then gives the relative magnetization of the two components at the selected velocity v. The measurement of the signal amplitude is defined by the amplitude of the echo of obtained by applying the 90° tipping pulse and a 180° refocusing pulse. This is an indication of the relative flow rates of the two components at the selected velocity. By repeating the measurements for different values of $\Delta t$, the velocity distribution of the two components can be obtained. The values of $T_{1,1}$ and $T_{1,2}$ needed can be measured separately. When it is desired to estimate flow rates of three fluids, three different pre-polarization lengths may be used.

Another way to differentiate the phases is to use a plurality of different lengths of measurement in the measurement section 110. If magnet lengths in the coil region are negligible compared to the overall flow length, the magnetic moment after the fluid leaves the prepolarization region decays according to the following equation:

$$M_i = M_{0,i}(1 - e^{-L_p/vT_{1,i}})e^{-L_1/vT_{2,i}} \quad (3)$$

Figure 7:
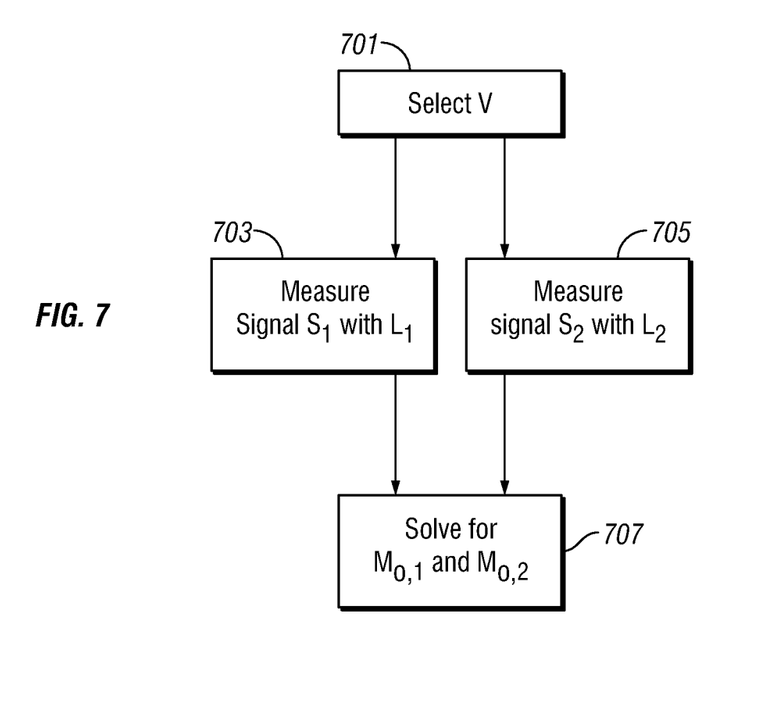
FIG. 7 shows a flowchart of a method of the present disclosure using two different measurement lengths.

This gives the relations $$S_1 = M_{0,1}(1 - e^{-L_p/vT_{1,1}})e^{-L_1/vT_{2,1}} + M_{0,2}(1 - e^{-L_p/vT_{1,2}})e^{-L_1/vT_{2,2}}$$

$$S_2 = M_{0,1}(1 - e^{-L_p/vT_{1,1}})e^{-L_2/vT_{2,1}} + M_{0,2}(1 - e^{-L_{p2}/vT_{1,2}})e^{-L_2/vT_{2,2}} \quad (4)$$

where $S_1$ and $S_2$ are signals measured with two different measurement lengths $L_1$ and $L_2$. This is illustrated in the flow chart of FIG. 7.

A velocity v is selected 701. This defines the value of $\Delta t$ used with a coil separation $L_1$ in the measurement section. For the value of $\Delta t$, a signal $S_1$ is measured 703 with the pre-polarization length $L_p$. For the same value of $\Delta t$, a signal $S_2$ is measured 705 with the same pre-polarization length $L_{p1}$ and coil separation $L_2$. Solution of the eqn. (4) 707 then gives the relative magnetization of the two components at the selected velocity v. This is an indication of the relative flow rates of the two components at the selected velocity. By repeating the measurements for different values of $\Delta t$, the velocity distribution of the two components can be obtained. The values of $T_{1,1}$ and $T_{1,2}$ needed can be measured separately.

A selected response signal may be related to one or more phases of the fluid. A typical multiphase fluid in petroleum exploration contains a hydrocarbon phase and a water phase. The water phase includes primarily water molecules and therefore primarily hydrogen and oxygen atoms. Thus, the water phase is responsive to an $^1H$ NMR excitation. Since carbon atoms are generally not present in the water phase, the water phase is generally unresponsive to $^{13}C$ NMR excitation. The hydrocarbon phase, on the other hand, includes molecules that are relatively rich in carbon atoms. Thus, the hydrocarbon phase is responsive to $^{13}C$ NMR excitations as well as to $^1H$ NMR excitations. Therefore, $^{13}C$ NMR response signals and $H^1$ NMR response signals may be used to determine water and hydrocarbon phase flow velocities and flow rates, as discussed below.

Where it is important to get the accurate estimate of oil or gas flow rates using a $^{13}C$ NMR response, the signal level from $^{13}C$ can be increased by using hyperpolarization. A suitable polarizing agent is added to the flow stream in the conduit 106. Several methods of hyperpolarization have been discussed in U.S. Pat. No. 7,126,332 to Blanz et al., having the same assignee as the present disclosure.

In one embodiment the polarizing agent is responsive to electron spin resonance, i.e. it contains atoms or molecules with unpaired electrons. The polarizing agent is added to the flow stream. In the magnet, the sample is first magnetized to thermal equilibrium. By subjecting the sample to high frequency (HF), meeting the ESR resonance condition, and making use of the Overhauser effect (OE), the polarization of the $^{13}C$ nuclei can be enhanced beyond equilibrium by a hyperpolarization factor of up to 2600 (theoretical maximum). Once the $^{13}C$ nuclei are hyperpolarized any known $^{13}C$ measurement can be executed by radiating the appropriate RF pulse sequence or by performing a CW NMR measurement at the $^{13}C$ resonance frequency. The amplitude of the received $^{13}C$ signals will be enhanced by the hyperpolarization factor.

In a second embodiment, the phenomenon of the Nuclear Overhauser Effect (NOE) is used to generate the hyperpolarization of the $^{13}C$ nuclei. The energy difference of the spin up and spin down states in $^1H$ is about 4 times of that of the energy difference of the two spin states in $^{13}C$. Analogous to the OE of the previous section the $^1H$ transition can be saturated (instead of the unbound electrons) by radiating RF at the $^1H$ resonance frequency. The $^1H$ spin system can couple to the spin system of $^{13}C$. The result is an increase in the population difference between spin up and spin down states of the $^{13}C$ system beyond the thermal equilibrium, i.e. the carbon nuclei are being hyperpolarized. Once the $^{13}C$ is hyperpolarized the $^{13}C$ NMR is processed with enhanced signal amplitude. The advantage of the described method is that hydrogen is usually present in any the flow stream. In contrast to OE no extra polarization agent needs to be used.

In a third embodiment, the polarizing agent can be polarized by optical pumping with circularly polarized light (most conveniently generated by a LASER) and making use of the Spin Induced Nuclear Overhauser Effect (SPINOE). The polarizing agent can be polarized in the agent chamber before being injected into the fluid sample. Alternatively it may be possible to polarize the polarizing agent after mixing with the formation fluid sample either still outside the magnet or inside. Different variants of optical pumping and SPINOE are needed depending on these alternatives (see below). Typically the polarizing agent is a noble gas with traces of other gases. In one instance, the polarizing agent can be xenon with traces of a vaporized alkali metal and nitrogen.

The discussion above is applicable to conduits in a variety of situations. One example would be the flow of fluids in a production well through production tubing. The production well may be producing hydrocarbons or may be a geothermal well in which a mixture of steam and water is produced. Another example is in the flow of produced hydrocarbons well to a collection point at the surface. The method discussed above may also be used to measure flow rate of drilling fluid. In an offshore well, the method may be used to measure the flow velocity of fluids coming up a riser.

Those versed in the art and having benefit of the present disclosure would also recognize that the principles disclosed herein may also be used for measurement of flow in an earth formation outside a cased borehole. The problem is discussed in U.S. Pat. No. 7,186,971 to Riley et al. having the same as in the as the present application. The method used by Riley uses a pulsed neutron source to irradiate fluids in the borehole in the earth formation and tracks the radiation with the fluid flow. The method described above may be used with a relatively minor modifications to track fluids outside the cased borehole. The modification comprises using a magnet for producing a magnetic field outside the cased borehole and making measurements on polarize nuclei in the fluid outside the borehole.

The processing of the data may be conveniently done on a processor. The processor executes a method using instructions stored on a suitable computer-readable medium product. The computer-readable medium may include a ROM, an EPROM, an EAROM, a flash memory, and/or an optical disk.

What is claimed is:

1. A method of estimating a flow rate of a phase of a fluid having a plurality of components, the method comprising:
    using a magnet for polarizing nuclei of the fluid flowing over a plurality of distances wherein a number of the distances is equal to or greater than a number of the components;
    measuring a magnetization of the polarized nuclei for each of the plurality of distances for a selected flow velocity;
    using the plurality of measured magnetizations for estimating a relative fraction of each of the plurality of components corresponding to the selected velocity;
    wherein measuring the magnetization of the polarized nuclei further comprises pulsing a first coil with a tipping pulse, pulsing a second coil with a refocusing pulse, and measuring an echo resulting from the refocusing pulse with a third coil.

2. The method of claim 1 wherein a time interval between the tipping pulse and the refocusing pulse is a defined by the selected velocity and a distance between the first coil and the second coil.

3. The method of claim 1 wherein the fluid is flowing in a conduit inside the magnet.

4. The method of claim 1 wherein the fluid is flowing in an earth formation outside the magnet.

5. The method of claim 1 further comprising pulsing the first coil and the second coil at a Larmor frequency corresponding to nuclei of $^1H$ and $^{13}C$.

6. The method of claim 1 wherein the fluid contains the nuclei of $^{13}C$, the method further comprising enhancing the polarization of the nuclei of $^{13}C$ using at least one of: (i) electron spin resonance, (ii) a Nuclear Overhauser Effect, and (iii) optical pumping and Spin Induced Nuclear Overhauser Effect.

7. An apparatus configured to estimate a flow rate of a phase of a fluid having a plurality of components, the apparatus comprising:
    a magnet configured to polarize nuclei of the fluid flowing over a plurality of distances wherein a number of the distances is equal to or greater than a number of the components;
    a coil arrangement configured to measure a magnetization of the polarized nuclei for each of the plurality of distances for a selected flow velocity, wherein the coil arrangement further comprises a first coil configured to pulse the polarized nuclei with a tipping pulse, a second coil configured to pulse the polarizing nuclei with a refocusing pulse, and a third coil configured to measure an amplitude of an echo resulting from the refocusing pulse;
    a processor configured to use the plurality of measured magnetizations to estimate a relative fraction of each of the plurality of components corresponding to the selected velocity.

8. The apparatus of claim 7 wherein a time interval between the tipping pulse and the refocusing pulse is a defined by the selected velocity and a distance between the first coil and the second coil.

9. The apparatus of claim 7 further comprising a conduit inside the magnet for conveying the fluid.

10. The apparatus of claim 9 wherein the conduit is selected from: (i) production tubing in a hydrocarbon producing well, (ii) production tubing in a geothermal well, (iii) a drilling tubular conveying drilling fluid, and (iv) a riser in offshore drilling.

11. The apparatus of claim 7 wherein the fluid is flowing in an earth formation outside the magnet.

12. The apparatus of claim 7 further comprising pulsing the first coil and the second coil at a Larmor frequency corresponding to nuclei of $^1H$ and $^{13}C$.

13. The apparatus of claim 7 wherein the fluid contains nuclei of $^{13}C$, the apparatus further comprising a device for enhancing the polarization of nuclei of $^{13}C$ in the fluid using at least one of: (i) electron spin resonance, (ii) a Nuclear Overhauser Effect, and (iii) optical pumping and Spin Induced Nuclear Overhauser Effect.

14. A method of estimating a flow rate of a phase of a fluid having a plurality of components, the method comprising:
    using a magnet for polarizing nuclei of the fluid flowing over a selected distance;
    pulsing the polarized nuclei with a tipping pulse with a first coil, a refocusing pulse with a second coil at a first distance from the first coil, a refocusing pulse with a third coil at a second distance from the first coil, and measuring an echo signal for each of the plurality of distances for a selected flow velocity;
    using the plurality of echo signals for estimating a relative fraction of each of the plurality of components corresponding to the selected velocity.

15. The method of claim 14 wherein a time interval between the tipping pulse and the refocusing pulse is defined by the selected velocity and a distance between the first coil and the second coil.

16. The method of claim 14 wherein the fluid is flowing in a conduit inside the magnet.

17. The method of claim 14 wherein the fluid is flowing in an earth formation outside the magnet.

18. The method of claim 14 further comprising pulsing the first coil and the second coil at a Larmor frequency corresponding to nuclei of $^1H$ and $^{13}C$.

19. The method of claim 14 wherein the fluid contains the nuclei of $^{13}C$, the method further comprising enhancing the polarization of the nuclei of $^{13}C$ using at least one of: (i) electron spin resonance, (ii) a Nuclear Overhauser Effect, and (iii) optical pumping and Spin Induced Nuclear Overhauser Effect.

20. An apparatus configured to estimate a flow rate of a phase of a fluid having a plurality of components, the apparatus comprising:
    a magnet configured to polarize nuclei of the fluid flowing over a selected distance;
    a first coil arrangement configured to pulse the polarized nuclei with a tipping pulse, a second coil at a first distance from the first coil configured to pulse the polarized nuclei with a refocusing pulse, the third coil at a second distance from the first coil configured to pulse the polarized nuclei with a refocusing pulse, and at least one additional coil configured to measure and echo signal for each of the plurality of distances for a selected flow velocity; and a processor configured to use the plurality of echo signals to estimate a relative fraction of each of the plurality of components corresponding to the selected velocity.

21. The apparatus of claim 20 wherein a time interval between the tipping pulse and the refocusing pulse is a defined by the selected velocity and a distance between the first coil and the second coil.

22. The apparatus of claim 20 wherein the fluid is flowing in a conduit inside the magnet.

23. The apparatus of claim 22 wherein the conduit is selected from: (i) production tubing in a hydrocarbon producing well, (ii) production tubing in a geothermal well, (iii) a drilling tubular conveying drilling fluid, and (iv) a riser in offshore drilling.

24. The apparatus of claim 20 wherein the fluid is flowing in an earth formation outside the magnet.

25. The apparatus of claim 20 further comprising pulsing the first coil and the second coil at a Larmor frequency corresponding to nuclei of $^1H$ and $^{13}C$.

26. The apparatus of claim 20 wherein the fluid contains nuclei of $^{13}C$, the apparatus further comprising a device for enhancing the polarization of nuclei of $^{13}C$ in the fluid using at least one of: (i) electron spin resonance, (ii) a Nuclear Overhauser Effect, and (iii) optical pumping and Spin Induced Nuclear Overhauser Effect.

* * * * *